United States Patent
Xiao et al.

(10) Patent No.: US 9,502,234 B2
(45) Date of Patent: Nov. 22, 2016

(54) METHODS TO PREPARE SILICON-CONTAINING FILMS

(71) Applicant: Air Products and Chemicals, Inc., Allentown, PA (US)

(72) Inventors: Manchao Xiao, San Diego, CA (US); Xinjian Lei, Vista, CA (US); Bing Han, Beijing (CN); Mark Leonard O'Neill, San Marcos, CA (US)

(73) Assignee: AIR PRODUCTS AND CHEMICALS, INC., Allentown, PA (US)

( * ) Notice: Subject to any disclaimer, the term of this patent is extended or adjusted under 35 U.S.C. 154(b) by 68 days.

(21) Appl. No.: 14/193,417

(22) Filed: Feb. 28, 2014

(65) Prior Publication Data

US 2015/0249007 A1    Sep. 3, 2015

Related U.S. Application Data

(63) Continuation-in-part of application No. 13/015,720, filed on Jan. 28, 2011, now Pat. No. 8,703,625.

(60) Provisional application No. 61/301,375, filed on Feb. 4, 2010.

(51) Int. Cl.

| C07F 7/02 | (2006.01) |
|---|---|
| H01L 21/02 | (2006.01) |
| B01J 19/00 | (2006.01) |
| C09D 183/04 | (2006.01) |
| C23C 16/30 | (2006.01) |
| C23C 16/44 | (2006.01) |
| H01L 21/316 | (2006.01) |
| H01L 29/00 | (2006.01) |

(52) U.S. Cl.
CPC .......... *H01L 21/02216* (2013.01); *B01J 19/00* (2013.01); *C07F 7/02* (2013.01); *C09D 183/04* (2013.01); *C23C 16/30* (2013.01); *C23C 16/44* (2013.01); *H01L 21/0228* (2013.01); *H01L 21/02164* (2013.01); *H01L 21/02274* (2013.01); *H01L 21/316* (2013.01); *H01L 29/00* (2013.01)

(58) Field of Classification Search
CPC ................. C07F 7/02; C01B 33/043
See application file for complete search history.

(56) References Cited

U.S. PATENT DOCUMENTS

| 4,579,965 | A | * | 4/1986 | Kanner | .................. | C07F 7/1876 |
| | | | | | | 556/479 |
| 5,177,234 | A | * | 1/1993 | Nguyen | .................. | C07F 7/045 |
| | | | | | | 556/470 |
| 5,204,141 | A | | 4/1993 | Roberts et al. | | |
| 5,344,804 | A | * | 9/1994 | Sjardijn | .................. | C08G 61/08 |
| | | | | | | 502/158 |
| 6,344,579 | B1 | * | 2/2002 | Fukumura | .................. | C07F 7/123 |
| | | | | | | 556/477 |
| 6,436,822 | B1 | | 8/2002 | Towle | | |
| 6,846,515 | B2 | | 1/2005 | Vrtis et al. | | |
| 7,105,460 | B2 | | 9/2006 | Kim et al. | | |
| 7,238,629 | B2 | * | 7/2007 | Shioya | .................. | C23C 16/401 |
| | | | | | | 257/760 |
| 7,777,131 | B2 | * | 8/2010 | Chatterton | .................. | H01B 7/288 |
| | | | | | | 174/119 C |
| 2003/0077883 | A1 | | 4/2003 | Ohtake | | |
| 2003/0100162 | A1 | | 5/2003 | Joo | | |
| 2004/0036123 | A1 | | 2/2004 | Keating et al. | | |
| 2004/0180551 | A1 | | 9/2004 | Biles et al. | | |
| 2006/0078676 | A1 | | 4/2006 | Lukas et al. | | |
| 2006/0183055 | A1 | | 8/2006 | O'Neill et al. | | |
| 2006/0247404 | A1 | | 11/2006 | Todd | | |
| 2007/0275166 | A1 | | 11/2007 | Thridandam et al. | | |
| 2008/0169450 | A1 | | 7/2008 | Chatterton et al. | | |
| 2008/0265381 | A1 | | 10/2008 | Afzali-Ardakani et al. | | |
| 2008/0271640 | A1 | | 11/2008 | Vrtis et al. | | |
| 2009/0075490 | A1 | | 3/2009 | Dussarrat | | |
| 2009/0090952 | A1 | | 4/2009 | Olsen et al. | | |
| 2009/0226609 | A1 | * | 9/2009 | Boisvert | .................. | C08G 77/56 |
| | | | | | | 427/226 |
| 2011/0215445 | A1 | * | 9/2011 | Yang | .................. | B01J 19/00 |
| | | | | | | 257/632 |
| 2013/0267653 | A1 | * | 10/2013 | Egawa | .................. | C08G 77/56 |
| | | | | | | 524/588 |
| 2013/0317184 | A1 | * | 11/2013 | Masi | .................. | C08F 10/02 |
| | | | | | | 526/113 |

FOREIGN PATENT DOCUMENTS

| CN | 1367205 | 9/2002 |
|---|---|---|
| CN | 1739190 | 2/2006 |
| CN | 1782124 | 6/2006 |
| CN | 101124605 | 2/2008 |
| CN | 101312129 | 11/2008 |
| CN | 101528974 | 9/2009 |
| EP | 0761841 | 6/2002 |
| EP | 1 246 239 A1 | 10/2002 |
| EP | 2 116 632 A2 | 11/2009 |
| JP | 6060408 | 8/1994 |
| JP | 2003158127 | 5/2003 |
| JP | 2004233254 A2 | 8/2004 |
| JP | 2005197561 | 7/2005 |
| JP | 2006237603 | 9/2006 |
| JP | 2007123633 | 5/2007 |
| JP | 2009147299 | 7/2009 |
| KR | 100262053 | 7/2000 |
| KR | 20050044797 A | 5/2005 |
| KR | 20060092118 A | 8/2006 |
| TW | 586204 | 5/2004 |
| WO | 2008048862 | 4/2008 |

* cited by examiner

*Primary Examiner* — Margaret Moore
(74) *Attorney, Agent, or Firm* — Michael K. Boyer

(57) ABSTRACT

Described herein are methods of forming dielectric films such as non-porous dielectric films, comprising silicon, oxide, and optionally nitrogen, carbon, hydrogen, and boron. Also disclosed herein are the methods to form dielectric films or coatings on an object to be processed, such as, for example, a semiconductor wafer. Specifically the methods include silanes that have bulky alkoxy groups as well as SiH groups. Examples of such silanes used in the methods including di-tert-pentoxysilane, di-tert-butoxysilane and silanes having the formula $(H)_2Si(OR)(OR^1)$ wherein R is tert-butyl and $R^1$ is selected from the group consisting of methyl, propyl, isopropyl, butyl, isobutyl, sec-butyl, pentyl, isopentyl, tert-pentyl and hexyl.

20 Claims, 8 Drawing Sheets

METHODS TO PREPARE SILICON-CONTAINING FILMS

CROSS REFERENCE TO RELATED APPLICATION

The present patent application is a continuation-in part-application from U.S. patent application Ser. No. 13/015,720 which claimed the priority benefit of prior U.S. Provisional Patent Application Ser. No. 61/301,375 filed Feb. 4, 2010.

BACKGROUND OF THE INVENTION

Disclosed herein are methods and compositions to prepare non-porous, silicon-containing materials or films, such as but not limited to, stoichiometric or non-stoichiometric silicon oxide, silicon oxynitride, or silicon oxycarbonitride films, for use in various electronic applications.

Thin films of silicon oxide are commonly used as dielectrics in semiconductor manufacturing because of their dielectric properties. In the manufacturing of silicon-based semiconductor devices, silicon oxide films can be used as gate insulations, diffusion masks, sidewall spacers, hard mask, anti-reflection coating, passivation and encapsulation, and a variety of other uses. Silicon oxide films are also becoming increasingly important for passivation of other compound semiconductor devices.

Other elements besides silica and oxygen may be present in silicon dioxide films. These other elements may sometimes be intentionally added into the compositional mixture and/or deposition process depending upon the resultant application of the film or desired end-properties. For example, the element nitrogen (N) may be added to the silicon oxide film to form a silicon oxynitride film that may provide a certain dielectric performance such as lower leakage current. The element germanium (Ge) may be added to the silicon oxide film to provide a Ge-doped silicon oxide that may reduce the deposition temperature of the film. Still other elements such as boron (B) or carbon (C) may be added to the silicon oxide film to increase the etch resistance. Depending upon the application, however, certain elements in the film may be undesirable even at lower concentration levels.

For example, when silicon dioxide films are used as etch stop or simply as dielectric layer under photoresists of deep-ultraviolet (DUV), small amounts of nitrogen in the film may interact with the DUV photoresist, chemically amplifying the material properties of the photoresist or poisoning the photoresist and rendering a portion of the photoresist insoluble in the developer. As a result, residual photoresist may remain on patterned feature edges or sidewalls of the structure. This may be detrimental to photolithographic patterning process of the semiconductor devices.

Another example of nitrogen free silicon oxide films can be found in the application of anti-reflection coatings (ARC). The ARC suppresses the reflections off of the underlying material layer during resist imaging thereby providing accurate pattern replication in the layer of energy sensitive resist. However, conventional ARC materials contain nitrogen such as, for example, silicon nitride and titanium nitride. The presence of nitrogen in the ARC layer may chemically alter the composition of photoresist material. The chemical reaction between nitrogen and the photoresist material may be referred to as "photoresist poisoning". Photoresist poisoned material that subjected to typical patterning steps could result in imprecisely formed features in the photoresist or excessive residual photoresist after patterning, both of which can detrimentally affect PR processes, such as etch processes. For example, nitrogen may neutralize acid near a photoresist and ARC interface and result in residue formation, known as footing, which can further result in curved or round aspects at the interface of the bottom and sidewalls of features rather than desired right angle.

For several applications, a plasma enhanced chemical vapor deposition process ("PECVD") is used to produce silicon oxide films at lower deposition temperatures than typical thermal chemical vapor deposition ("CVD") processes. Tetraethyloxysilane ("TEOS") having the molecular formula $Si(OC_2H_5)_4$ is a common precursor that can be used, in combination with one or more oxygen sources such as, but not limited to $O_2$ or $O_3$, for the PECVD deposition of silicon oxide films which have minimal residual carbon contamination. TEOS is supplied as a stable, inert, high vapor pressure liquid, and is less hazardous than other silicon-containing precursors such as $SiH_4$.

There is a general drive to move to lower deposition temperatures (e.g., below 400° C.) for one or more of the following reasons: cost (e.g., the ability to use cheaper substrates) and thermal budget (e.g., due to integration of temperature-sensitive high performance films). Further for PECVD TEOS films, the gap fill and conformality may be relatively better at lower temperatures. However, the film quality of the PECVD TEOS film may be poorer because the films do not have a stoichiometric composition, are hydrogen-rich, have a low film density, and/or exhibit a fast etch rate. Hence, there is a need for alternative precursors with better performance than TEOS.

BRIEF SUMMARY OF THE INVENTION

Described herein are methods of forming non-porous materials or films comprising silicon and oxygen that are free of critical elements such as nitrogen, carbon, halogens, and hydrogen, or, alternatively, comprises from about 0 to about 30 atomic weight percent of nitrogen and/or comprises from about 0 to about 30 atomic weight percent of carbon, as measured by X-ray photoelectron spectroscopy (XPS), and exhibit a % of non-uniformity of 5% or less. The % non-uniformity can be measured using the standard equation: % non-uniformity=((max−min)/(2*mean)). The films deposited using the method and precursors described herein are highly uniform without, in certain instances, relying on the assistance of a temperature, plasma, plasma-like method, or combinations thereof. Also disclosed herein are the methods to form dielectric films or coatings that are substantially free of nitrogen and/or substantially free of carbon, or alternatively contain relatively low amounts of nitrogen and carbon, on an object to be processed, such as, for example, a semiconductor wafer. Also described herein is the use of one or more silicon precursors having Formulae I through III described herein to form non-porous dielectric films.

In alternative embodiments, the method and precursor described herein can provide a material having a relatively low nitrogen content which provides a nitrogen-doped oxide material with a controlled composition. In alternative embodiments, the method and precursor described herein can provide a material having a relatively low carbon content which provides a carbon-doped oxide material with a controlled composition. In these embodiments, the material may comprise from about 0 to about 30 atomic weight percent nitrogen and/or carbon as measured by XPS. In certain embodiments, the precursors used are capable of making SiO₂ materials of very high purity, with non-detectable amounts of other elements including carbon, nitrogen, chlorine and halogens, and other species quantifiable by XPS.

In one aspect, there is provided a method for forming a film comprising silicon and oxygen on at least one surface of a substrate comprising:
provide the at least one surface of the substrate in a reaction chamber; and
forming the film on the at least one surface by a deposition process chosen from a chemical vapor deposition process and an atomic layer deposition process using a silicon precursor comprising at least one selected from the group of precursors having the following Formulas I, II, and III:

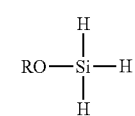

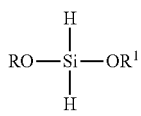

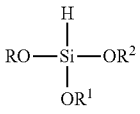

where R, R¹, and R² in Formulas I, II, and III are each independently an alkyl group, an aryl, an acyl group, or combinations thereof; and optionally an oxygen source wherein the dielectric film comprises from less than about 5 atomic % nitrogen or carbon as measured by XPS. In embodiments wherein the film comprises nitrogen or carbon, a nitrogen and/or carbon source may be also introduced during the forming step. In these embodiments, exemplary nitrogen sources including, but are not limited to, materials such as NH₃, N₂O, NH₂(CH₃), nitrogen plasma, a plasma comprising nitrogen and argon, a plasma comprising nitrogen and helium, a plasma comprising nitrogen and hydrogen, a plasma comprising ammonia, and combinations thereof may be introduced during the forming step and/or an additional introducing step. In these or other embodiments, the carbon source comprises a plasma comprising carbon dioxide. In a further embodiment, the carbon and nitrogen sources may be one in the same, such as, without limitation, NH₂(CH₃).

In another aspect, there is provided a method of forming a film comprising silicon and oxygen via an atomic layer deposition (ALD) process, the method comprising the steps of:
a. placing a substrate into an ALD reactor;
b. introducing into the reactor a silicon precursor comprising at least one selected from the group of precursors having the following Formulas I, II, and III:

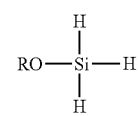

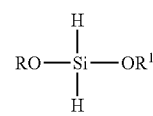

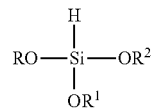

where R, R¹, and R² in Formulas I, II, and III are each independently an alkyl group, an aryl, an acyl group, or combinations thereof and optionally an oxygen source;
c. purging the ALD reactor with a gas;
d. introducing an oxygen source into the ALD reactor;
e. purging the ALD reactor with a gas; and
f. repeating the steps b through d until a desired thickness of the film is obtained wherein the dielectric film comprises less than about 5 atomic weight % carbon and/or nitrogen as measured by XPS.

In a further aspect, there is provided a method of forming a film comprising silicon oxide onto at least a surface of a substrate using an ALD or CVD process comprising:
a. placing a substrate into a reactor; and
b. introducing into the reactor a silicon precursor comprising at least one selected from the group of precursors having the following Formulas I, II, and III:

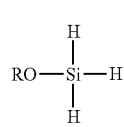

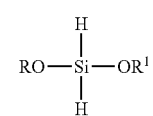

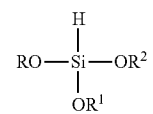

where R, R¹, and R² in Formulas I, II, and III are each independently an alkyl group, an aryl, an acyl group, or combinations thereof and optionally an oxygen source to deposit the film onto the at least one surface wherein the dielectric film comprises carbon and/or nitrogen from about 0 atomic weight % to about 30 atomic weight % as measured by XPS.

BRIEF DESCRIPTION OF SEVERAL VIEWS OF THE DRAWINGS

FIG. 4 shows that DTBOS deposited films had lower WER than TEOS films at all temperatures.

DETAILED DESCRIPTION OF THE INVENTION

Figure 1:
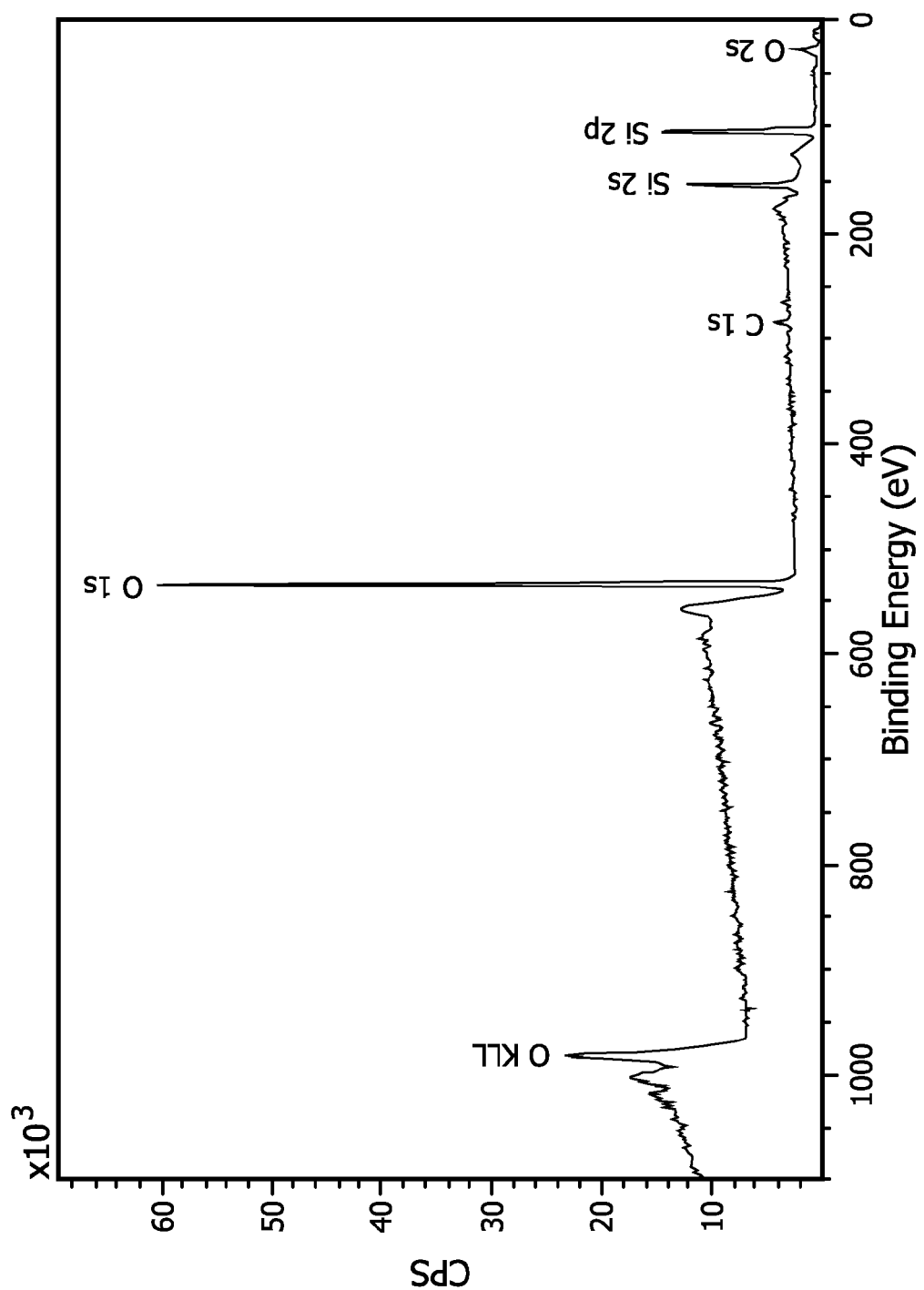
FIG. 1 provides the results of X-ray photoelectron spectroscopy (XPS) for a film deposited using the method described in Example 1.

Described herein is a method to form a highly uniform dielectric film (e.g., exhibits a % of non-uniformity of % of non-uniformity of 5% or less as measured using the standard equation: % non-uniformity=(max−min)/(2*mean). The dielectric films made using the method described herein generally predominantly contain silicon and oxygen. In certain embodiments, the dielectric film is substantially free of any other elements, such as nitrogen, carbon, chlorine and halogens, and hydrogen. The term "substantially free" as used herein means a film that comprises 2 atomic weight % or less of nitrogen as measured by XPS. In other embodiments, the dielectric film comprises other elements such as nitrogen and/or carbon in amounts ranging from about 2 atomic % to about 30 atomic %, and may contain other elements depending upon process conditions or additives used in the process. In certain embodiments, the method described herein does not require a plasma assist and/or is conducted at a low temperature (e.g., 600° C. or less). In an alternative embodiment, the method described herein is conducted using a low temperature (e.g., 450° C. or less) thermal process. The films described herein are dielectric films meaning that they typically exhibit a dielectric constant of 7 or less or 6 or less or 5 or less. In certain embodiments the materials produced may also contain elements such as boron, aluminium, and/or other elements that may contribute to a preferred feature of the material. These may be introduced into the process as elements of separate additives or as substituents of the main precursor.

In certain embodiments, one or more silicon precursors having Formulae I through III described herein can be used to form dielectric films that are non-porous or are substantially free of pores. In this regard, the dielectric films are formed in the absence of a pore-former precursor, porogen or carbon source.

The method used to form the dielectric films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits conformal films or materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the dielectric film is deposited using an ALD process. In another embodiment, the dielectric film is deposited using a CCVD process. In a further embodiment, the dielectric film is deposited using a thermal CVD process. In another embodiment, the precursor may condensed onto the substrate with minimal reaction taking place, followed by a post-treatment in order to render the material solid and aid in adhesion to the article being deposited on. It may be appreciated that there are many ways by which process conditions may be used to form a film from a chemical precursor, but that the final properties of the deposited material can be uniquely defined by the nature of the chemical precursor or additives used in combination with these precursors.

In certain embodiments, the method disclosed herein avoids pre-reaction of the precursors by using ALD or CCVD methods that separate the precursors prior to and/or during the introduction to the reactor. In this connection, deposition techniques such as an ALD or CCVD processes are used to deposit the dielectric film. In one embodiment, the film is deposited via an ALD process by exposing the substrate surface alternatively to the one or more the silicon-containing precursor, oxygen source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments, the precursor is introduced neat, or without additional reactants or additives, to condense, fill features, or planarize a surface, followed by a reactant step to make the precursor react or to form a solid. In certain embodiments, this process uses oxidation processes, catalysts, or other energy forms (chemical, thermal, radiative, plasma, photonic, or any other ionizing or non-ionizing radiative energy) to modify the precursor and optional additives to form a solid material.

To form dielectric films comprising silicon and oxygen that are substantially nitrogen-free, it is desirable that the silicon-containing precursor is free of nitrogen. It is also desirable, in certain embodiments, that the precursors be reactive enough to deposit a film at a relatively low temperature (e.g., 400° C. or less). Despite a desire for precursor reactivity, the precursor must also be stable enough to not degrade or change to any significant extent over time (e.g., less than 1% change per year) Further, in these or other embodiments, it is desirable that the deposition method be performed in the absence of plasma. Without being bound to theory, it is believed that the reactivity of substituted silanes toward oxidation is proportional to the number of hydrogen atoms that are connected to the silicon atom.

The method disclosed herein forms the dielectric film using a silicon-containing precursor wherein the silicon-containing precursor is selected from a silicon precursor comprising at least one selected from the group of precursors having the following Formulas I, II, and III:

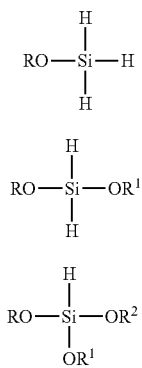

where R, R$^1$, and R$^2$ in Formulas I, II, and III are each independently an alkyl group, an aryl, an acyl group, or combinations thereof; optionally an additional silicon-containing precursor, optionally an oxygen source or reagent, and optionally a reducing agent. The selection of precursor materials for deposition depends upon the desired resultant dielectric material or film. For example, a precursor material may be chosen for its content of chemical elements, its stoichiometric ratios of the chemical elements, and/or the resultant dielectric film or coating that are formed under CVD. The precursor material may also be chosen for various other characteristics such as, for example, cost, stability, non-toxicity, handling characteristics, ability to maintain liquid phase at room temperature, volatility, molecular weight, or combinations thereof.

In one embodiment of the method disclosed herein, a dielectric film is formed using a silicon precursor comprising at least one selected from the group of precursors having the following Formulas I, II, and III:

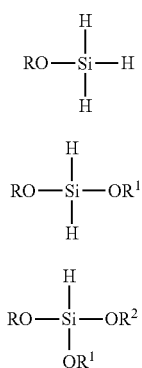

where R, R$^1$, and R$^2$ in Formulas I, II, and III are each independently an alkyl group, an aryl, an acyl group, or combinations thereof. In Formulas I through III and throughout the description, the term "alkyl" denotes a linear, branched, or cyclic functional group having from 1 to 20, or from 1 to 12 or from 1 to 6 carbon atoms. Exemplary alkyl groups include but are not limited to methyl, ethyl, propyl, isopropyl, butyl, isobutyl, sec-butyl, tert-butyl, pentyl, hexyl, octyl, decyl, dodecyl, tetradecyl, octadecyl, isopentyl, and tert-pentyl. In Formulas I through III and throughout the description, the term "aryl" denotes a cyclic functional group having from 6 to 12 carbon atoms. Exemplary aryl groups include but are not limited to phenyl, benzyl, tolyl, and o-xylyl.

In certain embodiments, one or more of the alkyl group, aryl group, and/or acyl group may be substituted or unsubstituted or have one or more atoms or group of atoms substituted in place of a hydrogen atom. Exemplary substituents include, but are not limited to, oxygen, sulfur, halogen atoms (e.g., F, Cl, I, or Br), nitrogen, boron, and phosphorous. In certain embodiments, the silicon-containing precursor having Formula I through III may have one or more substituents comprising oxygen atoms. In these embodiments, the need for an oxygen source during the deposition process may be avoided. In other embodiments, the silicon-containing precursor having Formula I through III has one of more substituents comprising oxygen atoms and also uses an oxygen source.

In certain embodiments, one or more of the alkyl groups, aryl groups, and/or acyl groups may be saturated or unsaturated. In embodiments wherein the one or more alkyl group or aryl group is unsaturated, it contains one or more double or triple bonds.

Examples of silicon-containing precursors having Formula I include: tertiarybutoxysilane, isopropoxysilane, ethoxysilane, n-butoxysilane, isobutoxysilane, methoxysilane, or phenoxysilane. Examples of silicon-containing precursors having Formula II include: di-tertiary-butoxysilane, diiso-propoxysilane, diethoxysilane, di-n-butoxysilane, diisobutoxysilane, dimethoxysilane, or diphenoxysilane. Examples of silicon-containing precursors having Formula III include: tri-tertiary-butoxysilane, triiso-propoxysilane, triethoxysilane, tri-n-butoxysilane, triiso-butoxysilane, trimethoxysilane, or triphenoxysilane. In one embodiment of the method described herein, the silicon-containing precursor comprises at least one of the following precursors:

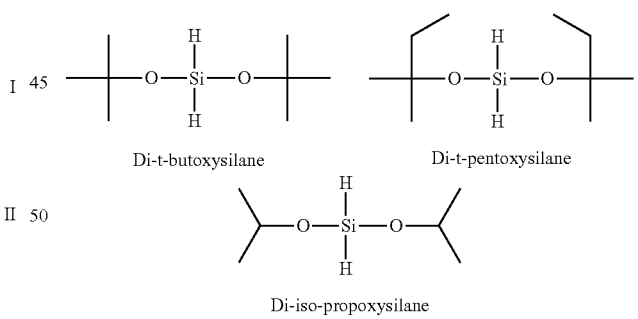

In one particular embodiment, the silicon-containing precursor comprises di-tert-butoxysilane.

In certain embodiments, the method described herein further comprises one or more additional silicon-containing precursors other than the silicon-containing precursor having the above Formulas I through III described above. Examples of additional silicon-containing precursors include, but are not limited to, organo-silicon compounds such as siloxanes (e.g., hexamethyl disiloxane (HMDSO) and dimethyl siloxane (DMSO)); organosilanes (e.g., methylsilane; dimethylsilane; vinyl trimethylsilane; trimethylsilane; tetramethylsilane; ethylsilane; disilylmethane; 2,4- disilapentane; 1,2-disilanoethane; 2,5-disilahexane; 2,2-disilylpropane; 1,3,5-trisilacyclohexane, and fluorinated derivatives of these compounds; phenyl-containing organo-silicon compounds (e.g., dimethylphenylsilane and diphenylmethylsilane); oxygen-containing organo-silicon compounds, e.g., dimethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4,6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5,7,9-pentamethylcyclopentasiloxane; hexamethoxydisiloxane, and fluorinated derivatives of these compounds; and nitrogen-containing organo-silicon compounds (e.g., hexamethyldisilazane; divinyltetramethyldisilizane; hexamethylcyclotrisilazane; dimethylbis(N-methylacetamido)silane; dimethylbis-(N-ethylacetamido)silane; bis(tertiary-butylamino)silane (BTBAS), bis(tertiary-butylamino)methylsilane (BTBMS), bis(N-methylacetamido)methylvivylsilane; bis(N-butylacetamido) methylvivylsilane; tris(N-phenylacetamido)methylsilane; tris(N-ethylacetamido) vinylsilane; tetrakis(N-methylacetamido)silane; bis (diethylaminoxy)diphenylsilane; tris(diethylaminoxy) methylsilane; and bis(trimethylsilyl)carbodiimide).

In certain embodiments, the silicon-containing precursor comprises a nitrogen-containing organosilicon precursor having at least one N—H fragment and at least one Si—H fragment. Suitable precursors containing both the N—H fragment and the Si—H fragment include, for example, bis(tert-butylamino)silane (BTBAS), tris(tert-butylamino) silane, bis(iso-propylamino)silane, tris(iso-propylamino)silane, and mixtures thereof. In one embodiment, the precursor has the formula $(^{R5}NH)_n Si^R{}_{6mH4-(n+m)}$ wherein $^{R5}$ and $^{R6}$ are the same or different and independently selected from the group consisting of alkyl, vinyl allyl, phenyl, cyclic alkyl, fluoroalkyl, and silylalkyl and wherein n is a number ranging from 1 to 3, m is a number ranging from 0 to 2, and the sum of "n+m" is a number that is less than or equal to 3. In another embodiment, the silicon-containing precursor comprises a hydrazinosilane having the formula $(R^7{}_2N—NH)_x SiR^8{}_y H_{4-(x+y)}$ wherein $R^7$ and $R^8$ are same or different and independently selected from the group consisting of alkyl, vinyl, allyl, phenyl, cyclic alkyl, fluoroalkyl, silylalkyls and wherein x is a number ranging from 1 to 2, y is a number ranging from 0 to 2, and the sum of "x+y" is a number that is less than or equal to 3. Examples of suitable hydrazinosilane precursors include, but are not limited to, bis(1,1-dimethylhydrazino)-silane, tris(1,1-dimethylhydrazino)silane, bis(1,1-dimethylhydrazino)ethylsilane, bis(1,1-dimethylhydrazino)isopropylsilane, bis(1,1-dimethylhydrazino)vinylsilane, and mixtures thereof. In certain embodiments, the precursor or additives further includes halogenated silanes, boranes, borazines, borates, and modified versions thereof.

Depending upon the deposition method, in certain embodiments, the one or more silicon-containing precursors may be introduced into the reactor at a predetermined molar volume, or from about 0.1 to about 1000 micromoles. In this or other embodiments, the silicon-containing precursor may be introduced into the reactor for a predetermined time period, or from about 0.001 to about 500 seconds.

As previously mentioned, some of the dielectric films deposited using the methods described herein may be formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $NO_2$, carbon monoxide (CO), carbon dioxide ($CO_2$) and combinations thereof. In certain embodiments, the oxygen source comprises an oxygen source gas that is introduced into the reactor at a flow rate typically ranging from about 1 to about 2000 standard cubic centimeters (sccm), the range thereof being dependent upon the reaction process, desired material, substrate size, deposition rate, and/or a variety of other factors. The oxygen source can be introduced prior to the precursor, concurrent with the precursor, sequentially with the precursor in a repeating cyclic fashion, or after all the precursor has been introduced. In one particular embodiment, the oxygen source comprises water. In embodiments wherein the film is deposited by an ALD or a cyclic CVD process, the precursor pulse can have a pulse duration that is greater than 0.01 seconds, and the oxygen source can have a pulse duration that is greater than 0.01 seconds, while the water pulse duration can have a pulse duration that is greater than 0.01 seconds. In yet another embodiment, the purge duration between the pulses that can be as low as 0.01 seconds or is continuously pulsed without a purge in-between.

The deposition methods disclosed herein may involve one or more purge gases. The purge gas, which is used to purge away unconsumed reactants and/or reaction byproducts, is in certain embodiments, an inert gas or non-reactive gas that does not react with the precursors. Exemplary purge gases include, but are not limited to, Ar, $N_2$, He, Xe, neon, $H_2$ and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

In certain embodiments, such as, for example, for those embodiments where the dielectric constant further comprises elements of nitrogen and/or carbon and/or other species, an additional gas such as a nitrogen source gas may be introduced into the reactor. Examples of additives may include, for example, NO, $NO_2$, ammonia, ammonia plasma, hydrazine, monoalkylhydrazine, dialkylhydrazine, hydrocarbons, heteroatomic hydrocarbons, boranes, borates, borazines, and combinations thereof.

In certain embodiments of the method described herein, the temperature of the reactor or a deposition chamber may range from ambient temperature (e.g., 25° C.) to about 700° C. Exemplary reactor temperatures for the ALD or CVD deposition include ranges having any one or more of the following endpoints: 25, 50, 75, 100, 125, 150, 175, 200, 225, 250, 275, 300, 325, 350, 375, 400, 425, 450, 475, 500, 525, 550, 575, 600, 625, 650, 675, or 700° C. Examples of particular reactor temperature ranges include but are not limited to, 25° C. to 375° C., or from 75° C. to 700° C., or from 325° C. to 675° C. In this or other embodiments, the pressure may range from about 0.1 Torr to about 100 Torr or from about 0.1 Torr to about 5 Torr. In one particular embodiment, the dielectric film is deposited using a thermal CVD process at a pressure ranging from 100 mTorr to 600 mTorr. In another particular embodiment, the dielectric film is deposited using an ALD process at a temperature range of 1 Torr or less.

In certain embodiments of the method described herein, the temperature of the substrate in the reactor or a deposition chamber, may range from ambient temperature (e.g., 25° C.) to about 700° C. Exemplary substrate temperatures for the ALD or CVD deposition include ranges having any one or more of the following endpoints: 25, 50, 75, 100, 125, 150, 175, 200, 225, 250, 275, 300, 325, 350, 375, 400, 425, 450, 475, 500, 525, 550, 575, 600, 625, 650, 675, or 700° C. Examples of particular substrate temperature ranges include but are not limited to, 25° C. to 375° C., or from 75° C. to 700° C., or from 325° C. to 675° C. In certain embodiments, the substrate temperature may be the same as or in the same temperature range as the reactor temperature during the deposition. In other embodiments, the substrate temperature differs from the reactor temperature during the deposition.

The respective step of supplying the precursors, the oxygen source, and/or other precursors, source gases, and/or reagents may be performed by changing the time for supplying them to change the stoichiometric composition of the resulting dielectric film.

Energy is applied to the at least one of the precursor, oxygen source, reducing agent, other precursors or combination thereof to induce reaction and to form the dielectric film or coating on the substrate. Such energy can be provided by, but not limited to, thermal, plasma, pulsed plasma, helicon plasma, high density plasma, inductively coupled plasma, X-ray, e-beam, photon, and remote plasma methods. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The silicon-containing precursors and/or other precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, leading to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

In one embodiment of the method described herein, a cyclic deposition process such as CCVD, ALD, or PEALD may be employed, wherein at least one silicon-containing precursor having Formulas I through III and combinations thereof and optionally an oxygen source such as, for example, ozone, oxygen plasma or water plasma are employed. The gas lines connecting from the precursor canisters to the reaction chamber are heated to one or more temperatures depending upon the process requirements and the container of the silicon-containing precursor having Formula I through III is injected into a vaporizer kept at one or more temperatures for direct liquid injection. A flow of argon and/or other gas may be employed as a carrier gas to help deliver the vapor of the at least one silicon-containing precursor to the reaction chamber during the precursor pulsing. In certain embodiments, the reaction chamber process pressure is about 1 Torr or less. In a typical ALD or CCVD process, the substrate such as a silicon oxide substrate is heated on a heater stage in a reaction chamber that is exposed to the silicon-containing precursor initially to allow the complex to chemically adsorb onto the surface of the substrate. A purge gas such as argon purges away unabsorbed excess complex from the process chamber. After sufficient purging, an oxygen source may be introduced into reaction chamber to react with the absorbed surface followed by another gas purge to remove reaction by-products from the chamber. The process cycle can be repeated to achieve the desired film thickness. In this or other embodiments, it is understood that the steps of the methods described herein may be performed in a variety of orders, may be performed sequentially or concurrently (e.g., during at least a portion of another step), and any combination thereof. The respective step of supplying the precursors and the oxygen source gases may be performed by varying the duration of the time for supplying them to change the stoichiometric composition of the resulting dielectric film.

In another embodiment of the method disclosed herein, the dielectric films is formed using a ALD deposition method that comprises the steps of:

a. introducing a silicon precursor comprising at least one selected from the group of precursors having the following Formulas I, II, and III:

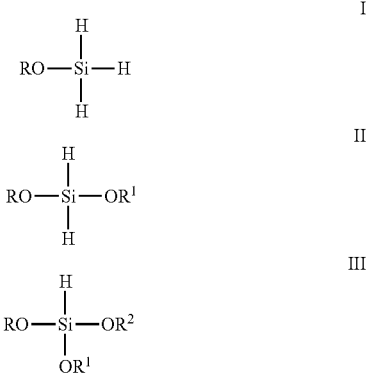

where R, $R^1$, and $R^2$ in Formulas I, II, and III are each independently an alkyl group, an aryl, an acyl group, or combinations thereof; and optionally an oxygen source, a nitrogen source, or combinations thereof and chemisorbing the at least one silicon precursor onto a substrate;

b. purging away the unreacted at least one silicon-containing precursor using a purge gas;

c. optionally introducing an oxygen source onto the heated substrate to react with the sorbed at least one silicon-containing precursor; and d. optionally purging away the unreacted oxygen source.

The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursor(s) and optionally oxygen source may be performed by varying the duration of the time for supplying them to change the stoichiometric composition of the resulting dielectric film.

For multi-component dielectric films, other precursors such as silicon-containing precursors, nitrogen-containing precursors, reducing agents, or other reagents can be alternately introduced into step "a" into the reactor chamber. In this embodiment, the reactor temperature may range from ambient to 600° C. In this or other embodiments, the pressure of the reactor may be maintained at 1 Torr or below.

In another aspect, there is provided a method of forming a film comprising silicon, oxygen, and nitrogen via an atomic layer deposition (ALD) process, the method comprising the steps of:
 a. placing a substrate into an ALD reactor;
 b. introducing into the reactor a silicon precursor comprising at least one selected from the group of precursors having the following Formulas I, II, and III:

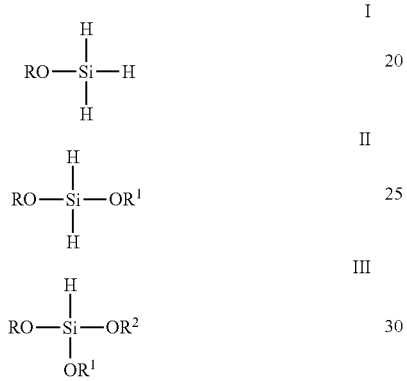

where R, $R^1$, and $R^2$ in Formulas I, II, and III are each independently an alkyl group, an aryl, an acyl group, or combinations thereof and optionally an oxygen source;
 c. purging the ALD reactor with a gas;
 d. introducing a nitrogen source into the ALD reactor;
 e. purging the ALD reactor with a gas;
 f. introducing an oxygen source into the ALD reactor;
 g. purging the ALD reactor with a gas wherein steps a to g are repeated until a desired thickness of the film is obtained. In this embodiment, exemplary nitrogen sources including, but are not limited to, materials such as $NH_3$, $N_2O$, organic amines such as methylamine ($NH_2(CH_3)$), ethylamine, diethylamine, iso-butylamine, tert-butylamine, nitrogen plasma, a plasma comprising nitrogen and argon, a plasma comprising nitrogen and helium, a plasma comprising nitrogen and hydrogen, a plasma comprising ammonia, and combinations thereof may be introduced during the forming step and/or an additional introducing step, such as a step h., and combinations thereof. The above steps define one cycle for the method described herein and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursor(s) and optionally oxygen or nitrogen source may be performed by varying the duration of the time for supplying them to change the stoichiometric composition of the resulting dielectric film. For multi-component dielectric films, other precursors such as silicon-containing precursors, nitrogen-containing precursors, reducing agents, or other reagents can be alternately introduced into step "a" into the reactor chamber. In this embodiment, the reactor temperature may range from ambient to 600° C., preferably from ambient to 400° C., most preferably ambient to 300° C.

In yet another aspect, there is provided a method of forming a film comprising silicon, oxygen, and nitrogen via an atomic layer deposition (ALD) process, the method comprising the steps of:
 a. placing a substrate into an ALD reactor;
 b. introducing into the reactor a silicon precursor comprising at least one selected from the group of precursors having the following Formulas I, II, and III:

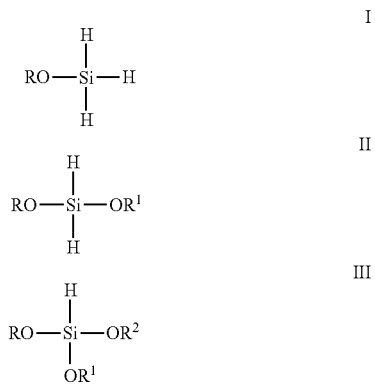

where R, $R^1$, and $R^2$ in Formulas I, II, and III are each independently an alkyl group, an aryl, an acyl group, or combinations thereof and optionally an oxygen source;
 c. purging the ALD reactor with a gas;
 d. introducing a nitrogen source into the ALD reactor; and
 e. purging the ALD reactor with a gas wherein steps a to e are repeated until a desired thickness of the film is obtained. In this embodiment, exemplary nitrogen sources including, but are not limited to, materials such as $NH_3$, $N_2O$, organic amines such as methylamine ($NH_2(CH_3)$), ethylamine, diethylamine, iso-butylamine, tert-butylamine, nitrogen plasma, a plasma comprising nitrogen and argon, a plasma comprising nitrogen and helium, a plasma comprising nitrogen and hydrogen, a plasma comprising ammonia, and combinations thereof may be introduced during the forming step and/or an additional introducing step and combinations thereof. The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursor(s) and optionally oxygen source may be performed by varying the duration of the time for supplying them to change the stoichiometric composition of the resulting dielectric film. For multi-component dielectric films, other precursors such as silicon-containing precursors, nitrogen-containing precursors, reducing agents, or other reagents can be alternately introduced into step "a" into the reactor chamber. In this embodiment, the reactor temperature may range from ambient to 600° C., preferably from ambient to 400° C., most preferably ambient to 300° C.

In a further embodiment of the method described herein, the dielectric film is deposited using a thermal CVD process. In this embodiment, the method comprises: placing one or more substrates into a reactor which is heated to a temperature ranging from ambient temperature to about 700° C. or from 400 to 700° C.; introducing a silicon precursor comprising at least one selected from the group of precursors having the following Formulas I, II, and III:

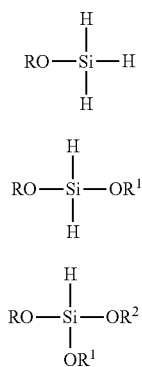

where R, $R^1$, and $R^2$ in Formulas I, II, and III are each independently an alkyl group, an aryl, an acyl group, or combinations thereof; and optionally a source selected from an oxygen source, a nitrogen source, or combinations thereof into the reactor to deposit a dielectric film onto the one or more substrates wherein the reactor is maintained at a pressure ranging from 100 mTorr to 600 mTorr during the introducing step. In certain embodiments, the pressure of the CVD reactor can be in the range of about 0.01 T to about 1T. The flow rate of the reactive gas such as, for example, $O_2$ can range from 5 sccm to 200 sccm. The flow rate of the one or more silicon-containing precursor vapor can range from 5 sccm to 200 sccm. The deposition temperature is the same as the reactor wall temperature. It can be in the range of ambient temperature to about 700° C. or from about 400° C. to about 700° C. The deposition time is pre-set for the process to yield films with a desired thickness. The deposition rate may be dependent one or more processing parameters including but not limited to the deposition temperature, the flow rate of $O_2$, the flow rate of carrier gas (He), the liquid mass flow of the silicon-containing precursor, the temperature of the vaporizer, and/or the pressure of the reactor. The vaporizer temperature can range from 20° C. to 150° C. The rate of the deposition of the material can be in the range of 0.1 nm to 1000 nm per minute. The rate can be controlled by varying any one of the following non-limiting parameters: deposition temperature, the vaporizer temperature, the flow of the LFC, the flow rate of the reactive additives and/or the pressure at the CVD reactor, for example.

In yet another embodiment, the method can be performed using a cyclic CVD process. In this embodiment, the same ALD reactor can be used for the cyclic CVD process. One of the differences in the cyclic CVD process to deposit uniform nitrogen free films from the ALD method described above is that the dosages of the silicon precursor and oxygen precursor can be greater than the dosages used for ALD, and thus the deposition rate can be much higher than ALD. The deposition temperature, may range from about ambient temperature to about 700° C. or from 400° C. to about 700° C.

In certain embodiments, the resultant dielectric films or coatings can be exposed to a post-deposition treatment such as, but not limited to, a plasma treatment, chemical treatment, ultraviolet light exposure, electron beam exposure, and/or other treatments to affect one or more properties of the film.

The dielectric films described herein have a dielectric constant of 7 or less. Preferably, the films have a dielectric constant of about 6 or below, or about 5 or below, or about 4 or below.

As mentioned previously, the method described herein may be used to deposit a dielectric film on at least a portion of a substrate. Examples of suitable substrates include but are not limited to, silicon, $SiO_2$, $Si_3N_4$, organosilica glass (OSG), fluorinated silica glass (FSG), silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes. The substrate may be uniform or patterned, smooth or having features, planar or non-planar.

The deposited dielectric films have applications which include but are not limited to computer chips, optical devices, magnetic information storages, coatings on a supporting material or substrate, microelectromechanical systems (MEMS), nanoelectromechanical systems, thin film transistor (TFT), and liquid crystal displays (LCD).

The following examples illustrate the method for preparing a dielectric film described herein and are not intended to limit it in any way.

EXAMPLES

In the following examples, unless stated otherwise, properties were obtained from sample films that were deposited onto medium resistivity (8-12 Ωcm) single crystal silicon wafer substrates. In the present study CVD depositions were performed using a low pressure chemical vapor deposition (LPCVD) horizontal furnace or an ATV PEO 612 furnace. The precursors were delivered to the furnace using vapor draw and line temperatures that were adjusted based on the vapor pressures for the precursor material. The Atomic Layer Deposition tool used for this study is an R&D designed horizontal tube furnace with attached environmental oven for heated precursor delivery. The system is capable of performing depositions from room temperature to 700° C. All plasma-based depositions were performed on an Applied Materials Precision 5000 system in a 200 mm DXZ chamber fitted with an Advanced Energy 2000 radio frequency (RF) generator, using a TEOS process kit.

In the following examples, thickness and optical properties such as refractive index of the dielectric films were performed using standard reflectometry or ellipsometry measurement system such as, for example, on a FilmTek 2000SE ellipsometer, and using well-known data fitting techniques The characterization of the chemical composition of the films is accomplished using a Physical Electronics 5000VersaProbe XPS Spectrometer, which is equipped with multichannel plate detectors (MCD) and an Al monochromatic X-ray source. The XPS data are collected using $Alk_\alpha$ X-ray excitation (25 mA and 15 kV). The low-resolution survey spectra are collected at 117 eV pass energy, 50 millisecond dwell time, and 1.0 eV/step. The high-resolution regional spectra are collected at 23.5 eV pass energy, 50 msec dwell time, 0.1 eV/step. The analysis area is 100 µm at a take-off-angle of 45°. The quantitative elemental analyses were determined by measuring the peak areas from the high-resolution regional spectra and applying the transmission-function corrected atomic sensitivity factors. A PHI Summitt software is used for data collection and CasaXPS software is used for data analysis. The etch rate is calibrated against 203 nm $SiO_2$/Si and is approximately 120 Å/min.

The etch test is carried out in 6:1 Buffered Oxide Etch ("BOE") solution which has a volume ratio of 6 parts 40% $NH_4F$ in water and 1 part 49% HF solution in water to form a buffered oxide etch. Exemplary dielectric films are placed in HF solution for 30 seconds, followed by rinsing in deionized (DI) water and drying before being measured again for the loss of the material during the etch. The process is repeated until the films are completely etched. The etch rate is then calculated from the slope of the etch time vs. thickness etched. The films, along with the comparative silicon oxide films, are measured for their thickness at 3 different points across the film surface before and after etch.

Fourier Transform Infrared Spectroscopy (FTIR) data was collected on the wafers using a Thermo Nicolet Nexus 470 system or similar system, equipped with a DTGS KBR detector and KBr beam splitter. Background spectra were collected on similar medium resistivity wafers to eliminate $CO_2$ and water from the spectra. Data was typically obtained in the range of from 4000 to 400 $cm^{-1}$ by collecting 32 scans with a resolution of 4 $cm^{-1}$. All films were commonly baseline corrected, intensities were normalized to a film thickness of 500 nm, and peaks areas and heights of interest were determined.

The dielectric constant of each sample film was determined according to ASTM Standard D150-98. Dielectric constants, k, are calculated from a C-V curve measured using, for example, a MDC 802B-150 Mercury Probe. It consists of a probe stage that holds the sample and forms electrical contacts on the film to be measured, a Keithley 236 source meter and HP4284A LCR meter for C-V measurement. Si wafers that have relatively low electrical resistivity (sheet resistance less than 0.02 ohm-cm) are used to deposit the films for C-V measurement. Front contact mode is used to form electrical contacts to the film. Liquid metal (mercury) is pushed out through a thin tube from a reservoir to the surface of the wafer to form two electrically conductive contacts. The contact areas are calculated based on the diameter of the tube from which the mercury is pushed out. The dielectric constant is then calculated from formula k=the capacitance×the contact area/the thickness of the film.

Example 1

Deposition of Silicon Oxide Films by Chemical Vapor Deposition Using Di-Tert-Butoxysilane (DTBOS)

Exemplary silicon oxide films were deposited using the precursors DTBOS and oxygen as the oxygen source. The deposition conditions for each film are provided in Table 1. The characteristics of each film are provided in Table 2.

TABLE 1

| Exemplary Film | Deposition Temp. (° C.) | Pressure (mtorr) | Precursor Flow Setting (%) | Precursor Flow (sccm) | Oxygen Flow (sccm) | Deposition Time (min.) |
|---|---|---|---|---|---|---|
| 1 | 550 | 250 | 30 | 14.11 | 20 | 50 |
| 2 | 650 | 250 | 30 | 14.11 | 40 | 50 |
| 3 | 600 | 500 | 30 | 12.67 | 40 | 99 |
| 4 | 650 | 500 | 30 | 13.46 | 40 | 99 |
| 5 | 650 | 250 | 30 | 14.26 | 40 | 99 |
| 6 | 650 | 250 | 30 | 10.46 | 40 | 30 | sccm = standard cubic centimeters per minute

TABLE 2

| Exemplary Film | Average Film Thickness (Å) | Film Thickness Uniformity | Refractive Index | Refractive Index Uniformity (%) | Deposition Rate (Å/min.) |
|---|---|---|---|---|---|
| 1 | 115 | 1.70 | 1.3318 | 6.0057 | 2.30 |
| 2 | 555 | 1.46 | 1.4733 | 0.2022 | 11.10 |
| 3 | 554 | 1.09 | 1.4734 | 0.2156 | 5.59 |
| 4 | 548 | 1.46 | 1.4719 | 0.2650 | 5.56 |
| 5 | 582 | 1.40 | 1.4448 | 0.2579 | 5.87 |
| 6 | 147 | 4.44 | 1.4249 | 3.0116 | 4.89 |

A typical XPS of one or the exemplary films from Example 1 that is highly uniform, high purity film free of elements, such as carbon and nitrogen, is shown in FIG. 1 and the composition of the different elements is also listed in Table 3. As can be seen from both FIG. 1 and Table 3, neither carbon nor nitrogen is detected in the films.

TABLE 3

Chemical Composition of the high purity Silicon Dioxide Film (in atomic %)
ND-quantities below detection limit

| Exemplary Film | Sputter depth (Å) | O | N | C | Si |
|---|---|---|---|---|---|
| 1 | 50 | 64.0 | ND | ND | 36.0 |
| 2 | 200 | 68.1 | ND | ND | 31.9 |
| 3 | 200 | 68.9 | ND | ND | 31.1 |
| 4 | 200 | 68.1 | ND | ND | 31.9 |

TABLE 3B

Chemical Composition of the Nitrogen Free Silicon Dioxide Film (in atomic %), corresponding to the spectra shown in FIG. 1.

| Elements | O | Si | C | N |
|---|---|---|---|---|
| Concentration | 64.2 | 34.1 | 1.5 | 0 |

Example 2

The Thickness Uniformity of the Film

Figure 2:
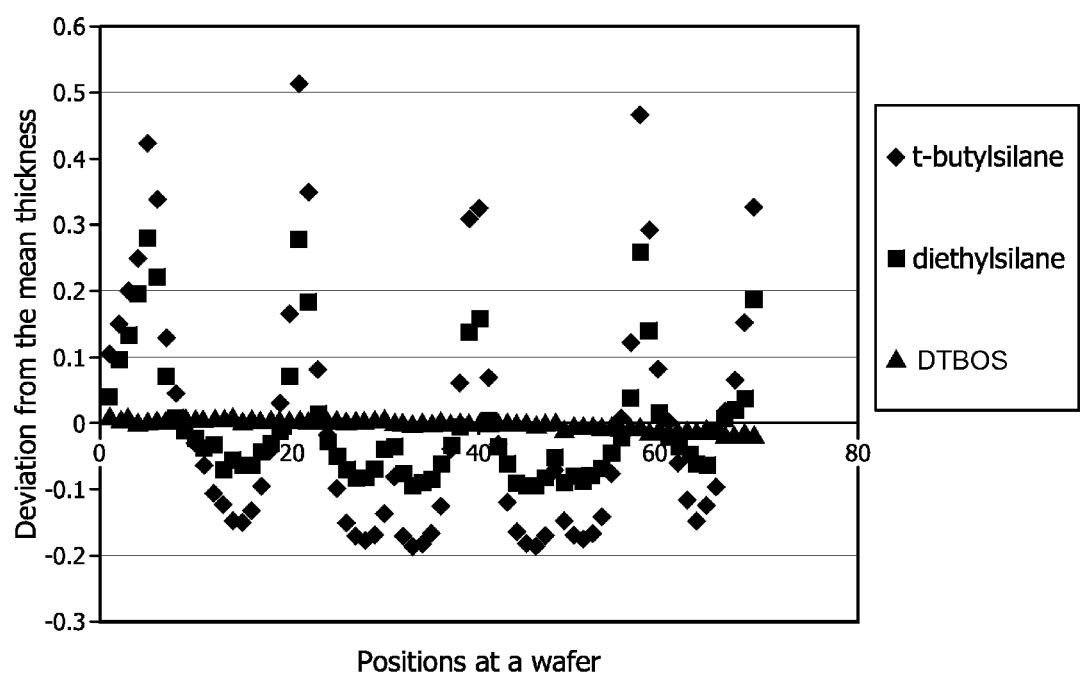
FIG. 2 provides the thickness uniformity for three exemplary films deposited using t-butyl silane, diethylsilane and di-tert-butoxysilane (DTBOS) in accordance with the method described in Example 2.

The nitrogen free silicon dioxide films formed using the methods and compositions described herein are measured for their thickness using an ellipsometer. In contrast to the poor uniformity of the nitrogen silicon dioxide films deposited using currently available methods, the films deposited using methods described in this invention show drastic improvement in the film uniformity within a substrate (or a wafer). A comparison in the film thickness uniformity between the films used the said invention and the ones used the existing methods is provided in FIG. 2 where the x-axis represents the position of measurement at a wafer substrate and y-axis represents the deviation of the thickness at each point from the average thickness of the film. It can be seen from FIG. 2 that the film deposited using the method described herein is much more uniform across the wafer substrates compared to other films.

A commonly used formula for thickness uniformity for the thin films, that is, The uniformity= (Maximum thickness−Minimum thickness)/ (2*Average)*100%

The thickness uniformity of the films formed using the method described herein is provided in Table 4. The results in Table 4 show that the film uniformity from the method described herein is more than 10 times better than the films formed using the existing methods (precursors).

TABLE 4

The Thickness Uniformity Of The Different Silicon Dioxide Films (%)

| Deposited with | di-tert-butoxysilane | t-butylsilane | Diethylsilane |
|---|---|---|---|
| Film uniformity | 1.43 | 35.0 | 18.74 |

Example 3

K and Dielectric Constant

Figure 3:
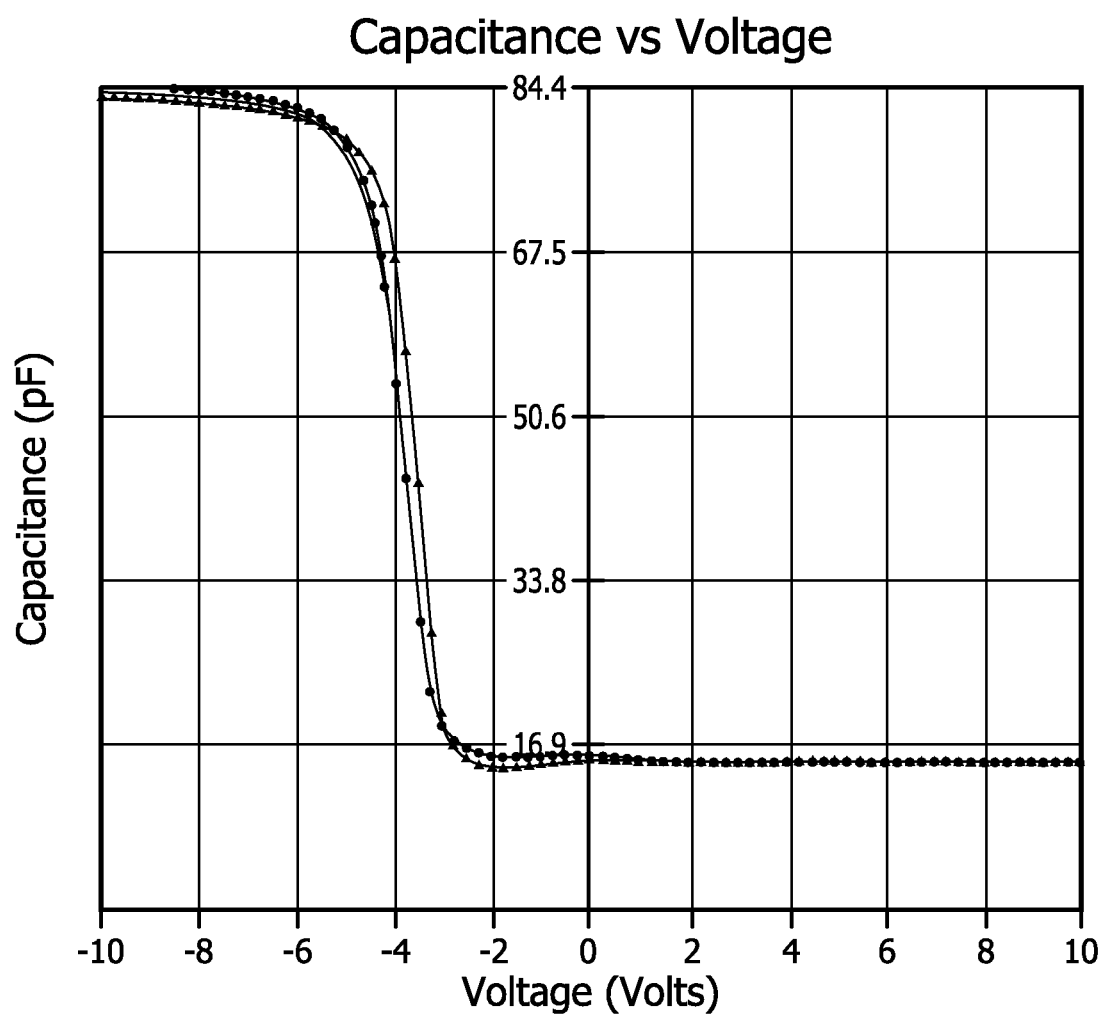
FIG. 3 provides the plot of the dielectric constant obtained from an exemplary film that was deposited using the precursor DTBOS described using one of the process conditions provided in Table 1.

The dielectric constant of the silicon oxide film formed using the method described herein is derived from the C-V plot shown in FIG. 3. For a known thickness of the film and contact area of the mercury probe used, the dielectric constant of the film is found to be 4.47.

Example 4

Comparison of Films Deposited by Plasma-Enhanced CVD Using Di-Tert-Butoxysilane Precursor and Tetraethyloxysilane Under Different Process Conditions In the following examples, unless stated otherwise, properties were obtained from sample films that were deposited onto medium resistivity (8-12 Ωcm) single crystal silicon wafer substrates. Deposition temperatures were 200, 300, and 400° C.

Table 5 provides a summary of the three different processing conditions that was used for comparing the precursors or di-tert-butoxysilane (DTBOS) and a comparative precursor tetraethyloxysilane (TEOS). The three different processing conditions are labeled BL-1, BL-2 and BL-3.

TABLE 5

| Process condition | BL-1 | BL-2 | BL-3 |
|---|---|---|---|
| Precursor flow (sccm) | 107 | 45 | 27 |
| He (carrier) | 1000 | 1000 | 1000 |
| O2 sccm) | 1100 | 1100 | 700 |
| Pressure (torr) | 8.2 | 8.2 | 3.5 |
| Spacing (mils) | 500 | 500 | 800 |
| Power density (W/cm2) | 2.27 | 2.27 | 0.87 |

Table 6 provides a comparison of K value, deposition rate and wet etch rate for TEOS vs. DTBOS for the BL1 condition. The deposition rate of DTBOS is higher than TEOS for the same volumetric flow of precursor. This shows that DTBOS may be more efficient than TEOS for PECVD deposition. Further, the WER of the DTBOS-deposited film is equal to or better than that or the TEOS-deposited films. This implies equal or better density of the $SiO_2$ films deposited using the DTBOS precursor.

TABLE 6

| | K value | | D/R (A/min) | | WER A/min, 6:1 BOE) | |
|---|---|---|---|---|---|---|
| T | TEOS | DTBOS | TEOS | DTBOS | TEOS | DTBOS |
| 200 | 4.99 | 5.78 | 5310 | 6174 | 4278 | 4096 |
| 300 | 4.43 | 4.55 | 4644 | 5200 | 2958 | 2844 |
| 400 | 4.21 | 4.16 | 3072 | 3714 | 2100 | 1888 |

Table 7 provides a comparison of K value, deposition rate and wet etch rate for TEOS vs. DTBOS deposited films using the BL2 processing condition. The deposition rate of DTBOS is higher than TEOS for the same volumetric flow of precursor. This proves the higher efficiency of the DTBOS precursor for PECVD deposition. However, the WER is equal or better than that for TEOS films. This implies equal or better density of the $SiO_2$ films formed from DTBOS.

TABLE 7

| | K value | | D/R (A/min) | | WER (A/min, 6:1 BOE) | |
|---|---|---|---|---|---|---|
| T | TEOS | DTBOS | TEOS D/R | DTBOS D/R | TEOS | DTBOS |
| 200 | 4.65 | 4.33 | 1201 | 1722 | 2958 | 2602 |
| 300 | 4.39 | 4.52 | 1003 | 1430 | 2304 | 1980 |
| 400 | 4.19 | 4.46 | 1045 | 1004 | 1840 | 1726 |

Table 8 provides a comparison of K value, deposition rate and wet etch rate for TEOS vs. DTBOS for the BL3 processing condition. The deposition rate of DTBOS is equivalent to TEOS for the same volumetric flow of precursor. However, the WER is clearly better than that for TEOS films. This implies better density of the SiO2 films formed from DTBOS. Also, the K values for DTBOS are lower, implying less moisture absorption.

TABLE 8

| | K value | | D/R (A/min) | | WER (A/min, 6:1 BOE) | |
|---|---|---|---|---|---|---|
| T | TEOS | DTBOS | TEOS | DTBOS | TEOS | DTBOS |
| 200 | 5.9 | 5.4 | 1014 | 1003 | 5382 | 4075 |
| 300 | 4.45 | 4.38 | 818 | 803 | 3504 | 3006 |
| 400 | 4.25 | 4.13 | 655 | 416 | 2340 | 2007 |

Figure 4:
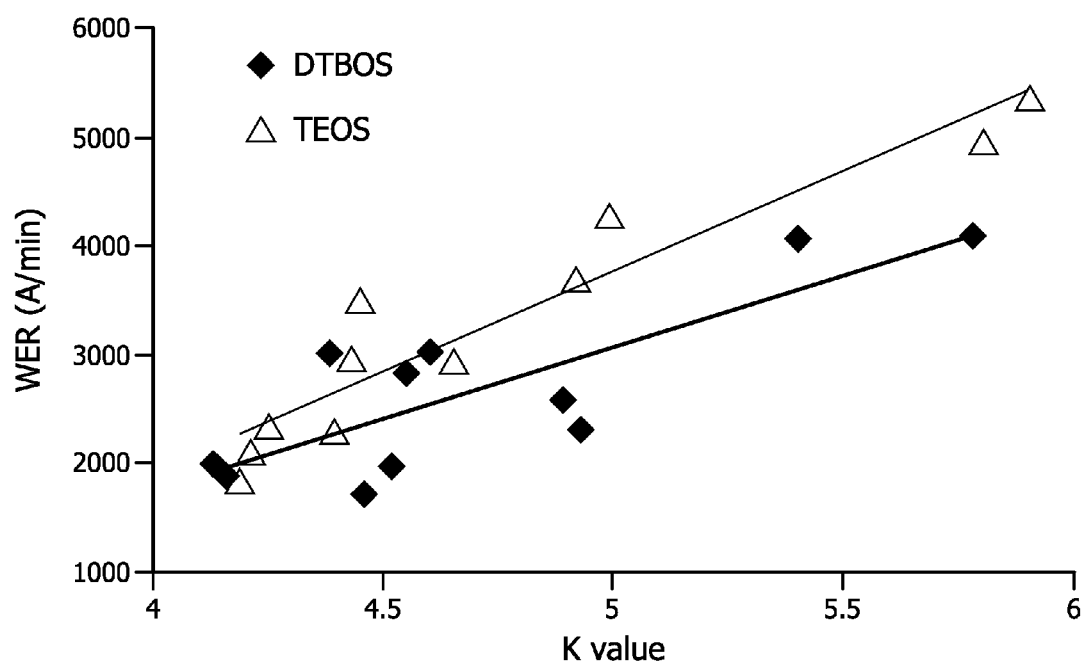
FIG. 4 shows a comparison of Wet Etch Rate (WER) of films deposited with BL1 condition described in the Examples at 3 different depositions temperatures or 400° C., 300° C., 200° C.

FIG. 4 shows a comparison of WER of films deposited using all of the baseline conditions and deposition temperatures described in Table 3 (e.g., BL-1, BL-2, and BL-3 and 200°, 300°, and 400° C.). DTBOS films have lower WER for the same K, implying higher density and higher quality oxide films. Thus, DTBOS can produce superior quality films to TEOS at relatively low temperatures for PECVD depositions.

Figure 5:
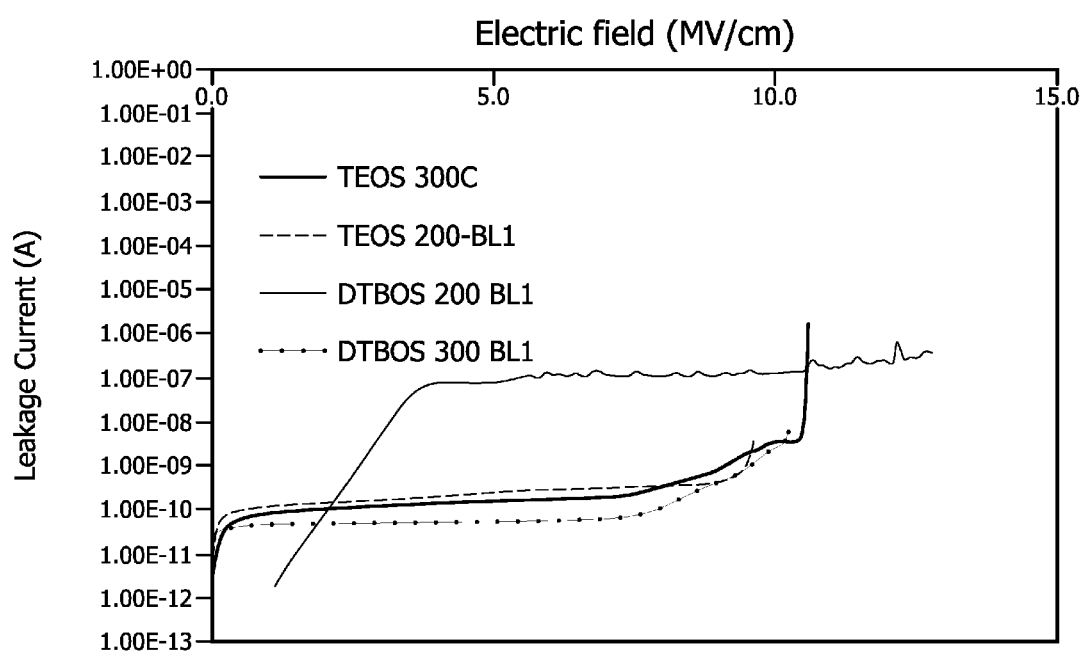
FIG. 5 provides the leakage current vs. electric field plots for TEOS vs. DTBOS at 200° C. and 300° C. depositions for the BL1 condition described in Table 3 of Example 4.
Figure 6:
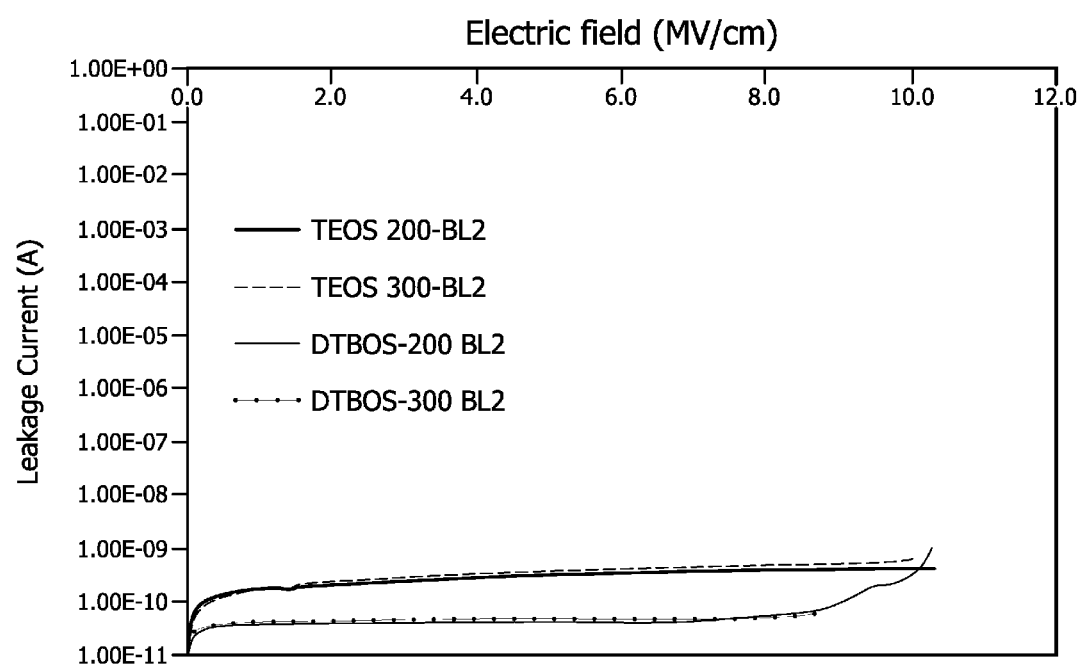
FIG. 6 provides the leakage current vs. electric field plots for TEOS vs. DTBOS at 200° C. and 300° C. depositions for the BL2 condition described in Table 3 of Example 4.
Figure 7:
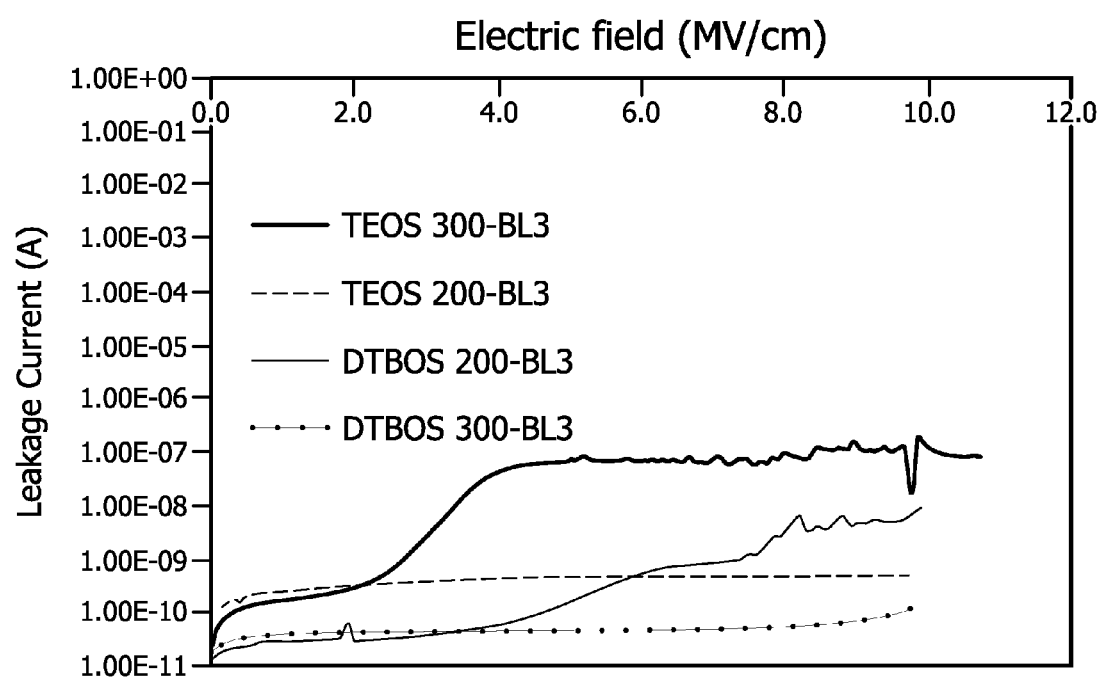
FIG. 7 provides the leakage current vs. electric field plots for TEOS vs. DTBOS at 200° C. and 300° C. depositions for the BL1 condition described in Table 3 of Example 4.

Table 9 below provides the breakdown voltage (Vbd) comparison of TEOS and DTBOS at different temperatures under process conditions BL1, BL2 and BL3 defined above in Table 5. In general, the breakdown voltages are 8-12 MV/cm, and are comparable between the two precursors. FIGS. 5, 6, and 7 show the leakage current vs. electric field plots for TEOS deposited films vs. DTBOS deposited films at 200° C. and 300° C. depositions.

FIG. 5 provides leakage current vs. electric field plots for TEOS vs. DTBOS at 200° C. and 300° C. depositions for BL1 condition. As DTBOS has higher K and WER at 200° C. than TEOS for BL1, the impact on film leakage is also seen. However, this is the only condition where DTBOS shows poorer leakage performance than TEOS. As seen with 300° C. data and with FIGS. 6 and 7, DTBOS $SiO_2$ leakage is generally superior to TEOS $SiO_2$ leakage.

FIG. 6 provides the leakage current vs. electric field plots for TEOS vs. DTBOS at 200° C. and 300° C. depositions for BL2 condition. Even though DTBOS has higher D/R; the leakage of DTBOS $SiO_2$ films are lower than that for TEOS, demonstrating excellent electrical quality and supporting the WER data.

FIG. 7 provides the leakage current vs. electric field plots for TEOS vs. DTBOS at 200° C. and 300° C. depositions for BL3 condition. Overall for BL3, leakage is lower with DTBOS than TEOS.

TABLE 9

|  | TEOS | DTBOS |
|---|---|---|
| BL1 | | |
| 200 C. | 9.6 | 12.7(leaky) |
| 300 C. | 9.68 | 10.26 |
| 400 C. | 7.9 | 9.26 |
| BL2 | | |
| 200 C. | 10.4 | 10.29 |
| 300 C. | 10.7 | 8.67 |
| 400 C. | 9.5 | 9.7 |
| BL3 | | |
| 200 C. | 10.9 | 9.89(leaky) |
| 300 C. | 9.7(leaky) | 9.74 |
| 400 C. | 9 | 9.61 |

Figure 8:
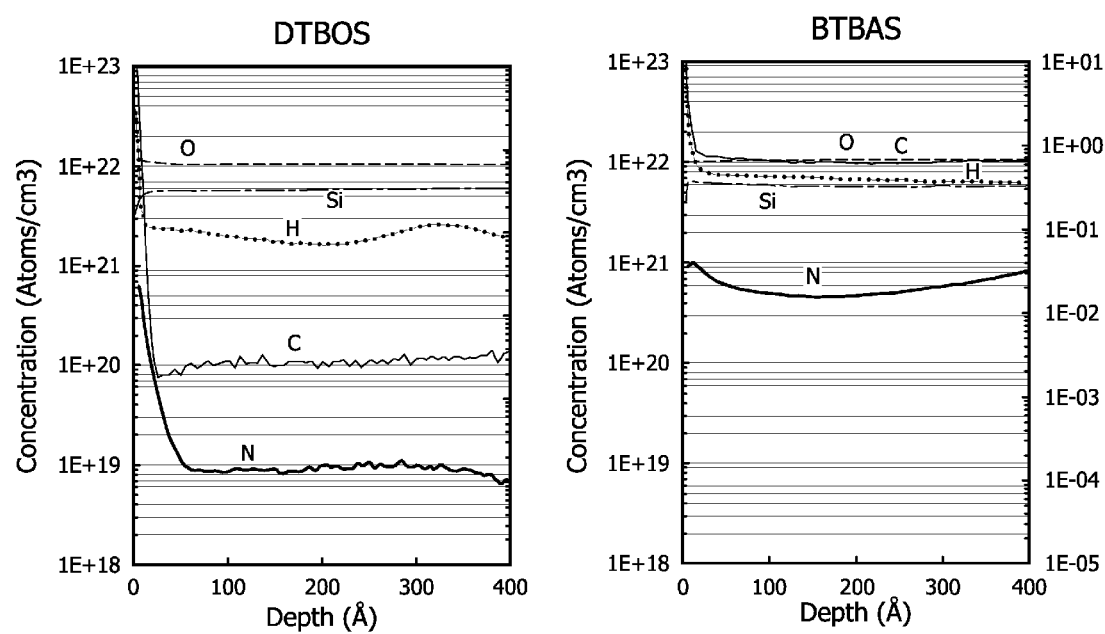
FIG. 8 provides dynamic secondary ion mass spectrometry data (D-SIMS) of DTBOS compared to bis(tertiarybutyl)aminosilane (BTBAS) in CVD films deposited from those precursors.

In FIG. 8 are provided dynamic secondary ion mass spectrometry data (D-SIMS) of DTBOS compared to bis (tertiarybutyl)aminosilane, (aka. BTBAS). It is known from XPS data for BTBAS, that CVD processes typically provide ~10 atomic % C (excluding hydrogen). This compares to Table 3 where carbon levels in DTBOS films are nondetectable. The D-SIMS data indicates approximately two orders of magnitude lower carbon content, suggesting that the actual carbon levels in these films, inferred from comparison to BTBAS XPS data, may be <0.1 atomic %.

ALD deposition data from DTBOS is provided in Table 10. Depositions of silicon oxide are demonstrated by the appropriate refractive index for these films.

TABLE 10

| Wafer Temp. | Source Pulse (seconds) | Ozone Pulse (seconds) | # of Cycles | Average Thickness (A) | Average RI | Angstroms/cycle | Uniformity (%) |
|---|---|---|---|---|---|---|---|
| 400 | 0.5 | 2.0 | 500 | 41 | 1.3379 | 0.0813 | 20.90 |
| 600 | 0.5 | 2.0 | 500 | 75 | 1.5547 | 0.1503 | 15.30 |
| 600 | 0.5 | 2.0 | 500 | 80 | 1.5425 | 0.1607 | 18.67 |
| 650 | 0.5 | 2.0 | 500 | 239 | 1.4365 | 0.4783 | 34.29 |
| 300 | 1.0 | 2.0 | 500 | 27 | 1.4457 | 0.0543 | 25.77 |
| 400 | 1.0 | 2.0 | 500 | 48 | 1.2477 | 0.0967 | 10.34 |
| 500 | 1.0 | 2.0 | 500 | 50 | 1.4343 | 0.1000 | 9.00 |
| 600 | 1.0 | 2.0 | 500 | 114 | 1.5324 | 0.2287 | 19.24 |
| 650 | 1.0 | 2.0 | 500 | 335 | 1.4574 | 0.6690 | 32.29 |
| 600 | 2.0 | 2.0 | 500 | 282 | 1.3983 | 0.5647 | 32.05 |
| 650 | 2.0 | 2.0 | 500 | 559 | 1.4476 | 1.1180 | 32.56 |

The present invention also includes a package with the reactants, as described above, comprising an electropolished stainless steel vessel with an inlet and an outlet having high purity low deadspace valves, containing tertiarybutoxysilane, isopropoxysilane, ethoxysilane, n-butoxysilane, isobutoxysilane, methoxysilane, phenoxysilane, di-tertiary-butoxysilane, diiso-propoxysilane, diethoxysilane, di-n-butoxysilane, diisobutoxysilane, dimethoxysilane, diphenoxysilane, tri-tertiary-butoxysilane, triiso-propoxysilane, triethoxysilane, tri-n-butoxysilane, triiso-butoxysilane, trimethoxysilane, or triphenoxysilane.

The reactants and methods of the present invention can be used to manufacture a device selected from the group consisting of: optical devices, magnetic information storages, coatings on a supporting material or substrate, microelectromechanical systems (MEMS), nanoelectromechanical systems, thin film transistor (TFT), and liquid crystal displays (LCD).

The invention claimed is:

1. A silicon precursor for depositing a film and having the following Formula II:

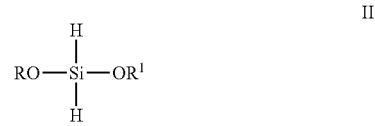

wherein both R and $R^1$ are tert-pentyl; or wherein R is tert-butyl and $R^1$ is selected from the group consisting of methyl, propyl, isopropyl, butyl, isobutyl, sec-butyl, pentyl, isopentyl, tert-pentyl, and hexyl.

2. The silicon precursor of claim 1 wherein both R and $R^1$ are tert-pentyl.

3. The silicon precursor of claim 1 wherein R is tert-butyl and $R^1$ is selected from the group consisting of methyl, propyl, isopropyl, butyl, isobutyl, sec-butyl, pentyl, isopentyl, tert-pentyl, and hexyl.

4. A method of forming a film comprising silicon, oxygen, and nitrogen, the method comprising the steps of:

a. placing a substrate into an ALD reactor;

b. introducing into the reactor a silicon precursor comprising at least one selected from the group of precursors having the following Formula II:

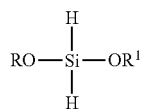

wherein both R and $R^1$ are tert-pentyl; or wherein R is tert-butyl and $R^1$ is selected from the group consisting of methyl, propyl, isopropyl, butyl, isobutyl, sec-butyl, pentyl, isopentyl, tert-pentyl, and hexyl; and optionally an oxygen source;
   c. purging the reactor with a purge gas;
   d. introducing a nitrogen source into the reactor;
   e. purging the reactor with a purge gas;
   f. introducing an oxygen source into the ALD reactor; and
   g. purging the ALD reactor with a purge gas, wherein steps b to g are repeated until a desired thickness of the film is obtained.

5. The method of claim 4 wherein the nitrogen source is at least one selected from the group consisting of $NH_3$, $N_2O$, organic amines such as methylamine ($NH_2(CH_3)$), ethylamine, diethylamine, iso-butylamine, tert-butylamine, nitrogen plasma, a plasma comprising nitrogen and argon, a plasma comprising nitrogen and helium, a plasma comprising nitrogen and hydrogen, a plasma comprising ammonia, and combinations thereof.

6. A method of forming a film comprising silicon, oxygen, and nitrogen, the method comprising the steps of:
   a. placing a substrate into an ALD reactor;
   b. introducing into the reactor a silicon precursor comprising at least one selected from the group of precursors having the following Formula II:

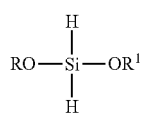

wherein both R and $R^1$ are tert-pentyl; or wherein R is tert-butyl and $R^1$ is selected from the group consisting of methyl, propyl, isopropyl, butyl, isobutyl, sec-butyl, pentyl, isopentyl, tert-pentyl, and hexyl; and optionally an oxygen source;
   c. purging the reactor with a purge gas;
   d. introducing a nitrogen source into the reactor; and
   e. purging the ALD reactor with a purge gas wherein steps b to e are repeated until a desired thickness of the film is obtained.

7. The method of claim 6 wherein the nitrogen source is at least one selected from the group consisting of $NH_3$, $N_2O$, an organic amines, nitrogen plasma, a plasma comprising nitrogen and argon, a plasma comprising nitrogen and helium, a plasma comprising nitrogen and hydrogen, a plasma comprising ammonia, and combinations thereof.

8. A method for forming a film on at least one surface of a substrate, the method comprising:
   providing the at least one surface of the substrate in a reaction chamber; and
   introducing into the reaction chamber a silicon precursor to form the film comprising at least one precursor selected from the group of precursors having the following Formula II:

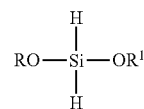

wherein both R and $R^1$ are tert-pentyl; or wherein R is tert-butyl and $R^1$ is selected from the group consisting of methyl, propyl, isopropyl, butyl, isobutyl, sec-butyl, pentyl, isopentyl, tert-pentyl, and hexyl; and
   introducing into the reaction chamber at least one source comprising an oxygen source wherein the at least one precursor and the at least one source react to form the film on the at least one surface of the substrate.

9. The method of claim 8 wherein at least one source further comprises a nitrogen source.

10. The method of claim 8 wherein the forming is at least one selected from cyclic chemical vapor deposition, plasma enhanced chemical vapor deposition, or atomic layer deposition.

11. The method of claim 8 wherein the silicon precursor further comprises di-tert-butoxysilane.

12. The method of claim 8 wherein the silicon precursor comprises di-tert-pentoxysilane.

13. The method of claim 9 wherein the oxygen source comprises oxygen.

14. The method of claim 9 wherein the oxygen source comprises ozone.

15. The method of claim 10 wherein the at least one source further comprises a nitrogen source.

16. The method of claim 9 wherein the nitrogen source is one selected from the group consisting of $NH_3$, $N_2O$, $NH_2(CH_3)$, nitrogen plasma, a plasma comprising nitrogen and argon, a plasma comprising nitrogen and helium, a plasma comprising nitrogen and hydrogen, a plasma comprising ammonia, and combinations thereof.

17. A method of forming a non-porous dielectric film comprising silicon and oxygen via an atomic layer deposition process, the method comprising the steps of:
   a. placing a substrate into an ALD reactor;
   b. introducing into the ALD reactor a silicon precursor comprising at least one selected from the group of precursors having the following Formula II:

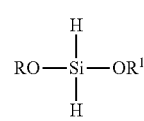

wherein both R and $R^1$ are tert-pentyl; or wherein R is tert-butyl and $R^1$ is selected from the group consisting of methyl, propyl, isopropyl, butyl, isobutyl, sec-butyl, pentyl, isopentyl, tert-pentyl, and hexyl;
   c. purging the ALD reactor with a gas;
   d. introducing an oxygen source into the ALD reactor;
   e. purging the ALD reactor with the gas; and
   f. repeating the steps b through e until a desired thickness of the non-porous dielectric film is obtained wherein the dielectric film comprises from up to about 30 atomic weight % nitrogen as measured by XPS.

18. The method of claim 17 wherein a nitrogen source thereof is introduced into the ALD reactor.

19. The method of claim 17 using a thermal CVD process, wherein the dielectric film comprises up to about 30 atomic weight % nitrogen as measured by XPS.

20. An electropolished stainless steel vessel with an inlet and an outlet having high purity low deadspace valves, comprising at least one silicon precursor having a formula II:

wherein both R and $R^1$ are tert-pentyl; or wherein R is tert-butyl and $R^1$ is selected from the group consisting of methyl, propyl, isopropyl, butyl, isobutyl, sec-butyl, pentyl, isopentyl, tert-pentyl, and hexyl.

* * * * *